United States Patent [19]

Columbus et al.

[11] Patent Number: 4,902,624
[45] Date of Patent: Feb. 20, 1990

[54] TEMPERATURE CYCLING CUVETTE

[75] Inventors: Richard L. Columbus, Rochester; Jeffrey L. Helfer; Johannes J. Porte, both of Webster; Jeffrey A. Wellman, Rochester, all of N.Y.

[73] Assignee: Eastman Kodak Company, Rochester, N.Y.

[21] Appl. No.: 273,781

[22] Filed: Nov. 21, 1988

Related U.S. Application Data

[63] Continuation-in-part of Ser. No. 270,385, Nov. 9, 1988, abandoned, which is a continuation of Ser. No. 123,751, Nov. 23, 1987, abandoned.

[51] Int. Cl.$^4$ ............................................. C12M 1/02
[52] U.S. Cl. ................................... 435/316; 435/296; 422/102; 356/246
[58] Field of Search ............... 435/287, 292, 296, 316; 356/246; 220/86 R; 215/1 R, 1 C; 422/58, 61, 102, 103, 104; 137/588

[56] References Cited

U.S. PATENT DOCUMENTS

| | | | |
|---|---|---|---|
| 3,994,594 | 11/1976 | Sandrock et al. | 422/102 |
| 4,683,195 | 7/1987 | Mullis et al. | 435/6 |
| 4,683,202 | 7/1987 | Mullis | 435/91 |
| 4,722,463 | 2/1988 | Anderson | 132/588 |

FOREIGN PATENT DOCUMENTS

| | | | |
|---|---|---|---|
| 2318475 | 10/1973 | Fed. Rep. of Germany | 422/102 |
| 3201691 | 9/1983 | Fed. Rep. of Germany | 422/102 |

Primary Examiner—Noah P. Kamen
Attorney, Agent, or Firm—Dana M. Schmidt

[57] ABSTRACT

There is disclosed a thermal cycling cuvette constructed with an improved sample fluid thermal time constant. The fluid surface-to-volume ratio, and the cuvette thermal path length and thermal resistance of at least one of the walls that provides a major surface of contact, are selected to provide such a thermal time constant that is no greater than about 10 seconds for a cuvette volume no greater than about 200 μl. Also included in the cuvette are means permitting the introduction and removal of liquid into and from the cuvette. A preferred construction permits ready and substantially complete removal of the liquid.

26 Claims, 9 Drawing Sheets

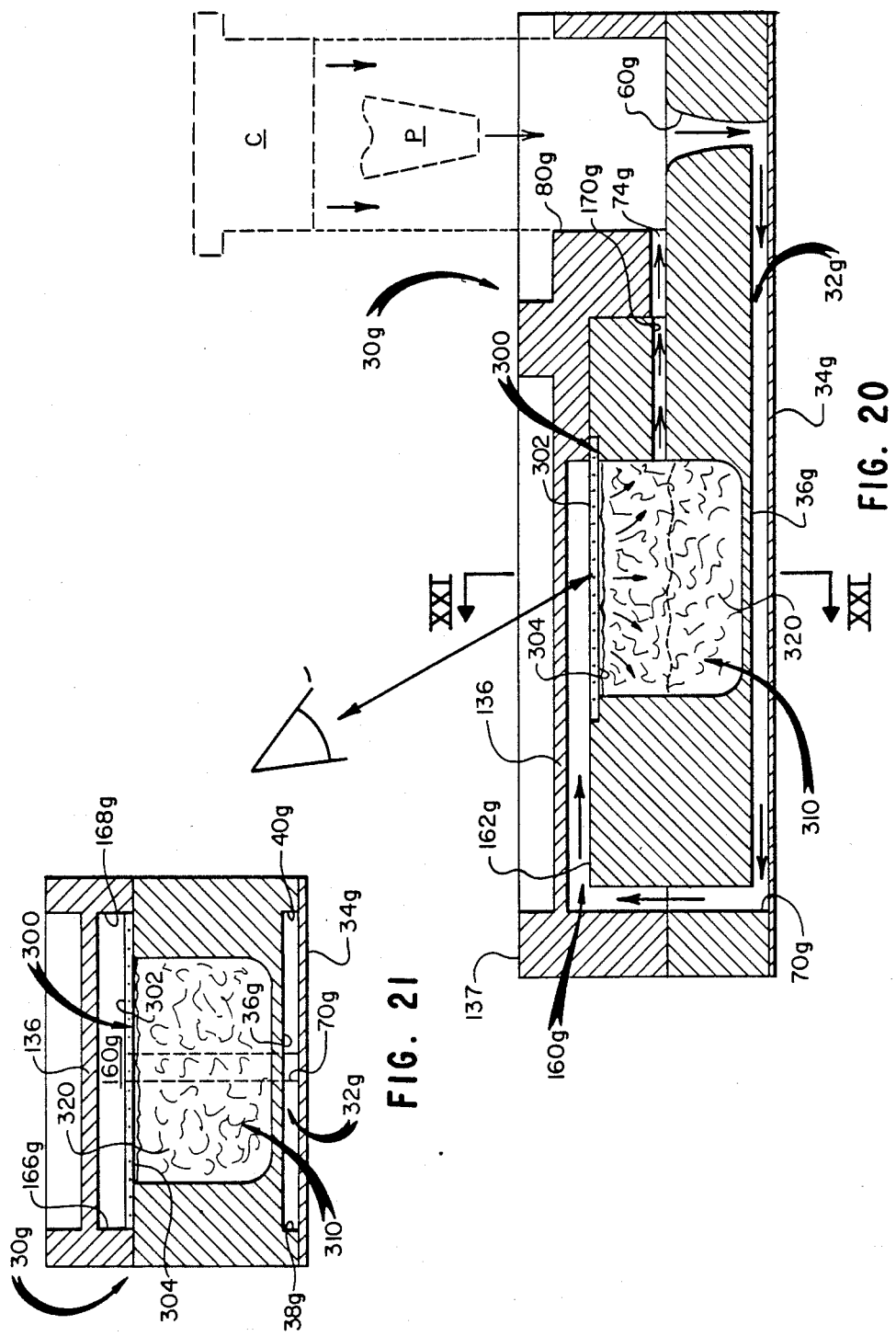

TEMPERATURE CYCLING CUVETTE

RELATED APPLICATIONS UNDER 35 U.S.C. SEC. 120

This is a continuation-in-part application of U.S. Ser. No. 270,385 filed on Nov. 9, 1988, now abandoned, which is a continuation of Ser. No. 123,751 filed on Nov. 23, 1987, now abandoned.

FIELD OF THE INVENTION

This invention relates to cuvettes in which reactions are undertaken in liquids confined within the cuvette, and particularly those reactions requiring carefully controlled temperatures, limited amount of sample, and a rapid rate of fluid temperature change.

BACKGROUND OF THE INVENTION

Although this invention is not limited to cuvettes used for nucleic acid amplification, the background is described in the context of the latter.

Nucleic acid amplification generally proceeds via the following steps (shown in FIG. 1):

(1) If DNA is to be amplified, a complete DNA double helix is optionally chemically excised, using an appropriate restriction enzyme(s), to isolate the region of interest.

(2) A solution of the isolated nucleic acid portion (here, DNA) and nucleotides is heated to and maintained at 92°–95° C. for a length of time, e.g., no more than about 10 minutes, to denature the two nucleic acid strands: i.e., cause them to unwind and separate and form a template.

(3) The solution is then cooled through a 50°–60° C. zone to cause a primer nucleic acid strand to anneal or "attach" to each of the two template strands. To make sure this happens, the solution is held at an appropriate temperature, such as about 55° C. for about 15 seconds, in an "incubation" zone.

(4) The solution is then heated to and held at about 70° C., to cause an extension enzyme, preferably a thermally stable enzyme such as a polymerase isolated from *thermus aquaticus*, to extend the primer strand bound to the template strand, by using the nucleotides that are present.

(5) The completed new pair of strands is heated to 92°–95° C. again, for about 10–15 seconds, to cause this pair to separate.

(6) Steps (3)–(5) are then repeated, a number of times until the appropriate number of strands are obtained. (See, e.g., U.S. Pat. No. 4,683,202 for further illustration.) The more repetitions, the greater the number of multiples of the nucleic acid (here, DNA) that is produced. Preferably the desired concentration of nucleic acid is reached in a minimum amount of time.

A cuvette is usually used to hold the solution while it passes through the aforementioned temperature stages. Depending upon the design given to the cuvette, it can proceed more or less rapidly through the various stages. A key aspect controlling this is the thermal transfer efficiency of the cuvette—that is, its ability to transfer heat more or less instantaneously to or from all of the liquid solution within the cuvette. The disposition and the thermal resistance of the liquid solution itself are the major aspects affecting the thermal transfer, since portions of the liquid solution that are relatively far removed from the heat source or sink, will take longer to reach the desired temperature.

The crudest and earliest type of cuvette used in the prior art is a test tube, which has poor thermal transfer efficiency since (a) the walls of the cuvette by being glass or plastic, do not transfer thermal energy well, and (b) a cylinder of liquid has relatively poor thermal transfer throughout the liquid. That is, not only does the liquid have low thermal conductivity, but also a cylinder of liquid has a low surface to volume ratio, that is, about 27 $in^{-1}$ for a fill of about 100 $\mu l$.

Still another problem in DNA amplification is the manner in which the cuvette allows for ready removal of the liquid after reaction is complete. A test tube configuration readily permits such removal. However, modification of the cuvette to provide better thermal transfer efficiency tends to reduce the liquid transferability.

Recent cuvette or vessel constructions for reaction of liquid are shown in U.S. Pat. Nos. 4,426,451 issued Jan. 17, 1984 and 3,691,017 issued on Sept. 12, 1972. In the former, little attempt is made to provide high thermal transfer efficiency, except that the liquid is distributed as a thin film that will allow rapid heating, if heat penetrates to the liquid. However, no mention is made of the cuvette being constructed of metal or any material that is highly thermally conductive. Furthermore, since the spacing between top and bottom walls is no greater than 125 microns to provide a strong capillary effect, removal of liquid from such cuvette will be difficult. At best, not all the liquid will be removed because of the strong capillary attraction.

In the case of cuvettes of U.S. Pat. No. 3,691,017, more features suitable for DNA amplification are provided. For example, by having a spacing of about 5 mm between major surfaces 23 and 24, it is more readily possible to remove all of the liquid, there being less capillary attraction left at such a gross spacing. In addition, a metal layer 38A is provided on the outside of the cuvette to provide contact with a heating device. However, this cuvette does not have a low thermal time constant for several reasons. One reason is that to ensure transparency, the surfaces 23 and 24 are not constructed of metal, but rather of an insulator. As a result, a long thermal transfer path is needed by extending metal 38A around the edge of the device and into only a portion 35 of the volume of the cuvette. This thermal path length is well in excess of 0.5 mm since it is much more than the thickness of the wall providing the major surface 23 or 24. Indeed, only a portion of the volume of the cuvette is in direct contact with the metallic thermal-energy transfer element.

Secondly, and more importantly, there is a high thermal resistance in the cuvette of the '017 patent because of the low fluid surface/volume ratio provided by cavity geometry, discussed hereinafter in detail.

OTHER RELATED APPLICATIONS

A commonly-owned application entitled "Detection of a Specific Nucleic Acid Sequence Using A Solid Phase Capture Means" has been cofiled with this application by Brent A. Burdick et al. That application describes a method for the detection of a specific nucleic acid sequence in a sample containing one or more nucleic acids, including the use of single-stranded, oligonucleotide primers complementary to the sequence, a labeled probe and known amplication techniques to form primer extension products of the primers. One of the primers is labeled with a specific binding moiety which, at some point in the method, is irreversibly complexed with a receptor thereto. The receptor is covalently bound to a solid support material, such as polymeric particles.

SUMMARY OF THE INVENTION

We have constructed a cuvette with rapid thermal transfer characteristics, as measured by its thermal time constant when filled with the liquid of choice. As such, it is ideally suited for replication of portions of DNA.

More specifically, in accord with one aspect of the invention, there is provided a thermal cycling cuvette for controlled reaction of components of a liquid involving cycling through a temperature range of at least about 35° C. (e.g. between 55° C. and about 90° C.), the cuvette having at least one liquid-confining chamber defined by two spaced-apart opposing walls, side walls connecting said two opposing walls, and means permitting the introduction of liquid into, and the removal of such liquid from, the chamber. The cuvette is improved in that the opposing walls and the side walls are dimensioned to provide (a) a spacing between said opposing walls of no less than 0.5 mm and (b) a predetermined surface-to-volume ratio of the chamber, at least one of the opposing walls being provided with a predetermined thermal path length abd thermal resistance, such that the ratio, path length and thermal resistance are effective to provide, for pure water contained within the chamber in contact with the opposing walls, a thermal time constant for the water that is no greater than about 10 seconds, for a liquid volume of no greater than about 200 µl.

In accord with another aspect of the invention, the cuvette is improved in that the permitting means noted in the previous paragraph includes a liquid access aperture, an air vent, and a movable valve for selectively sealing off fluid flow between (a) each of the access aperture and air vent, and (b) the chamber.

In accord with still another aspect of the invention, there is provided a cuvette for controlled reaction of components of a liquid, the cuvette having first and second liquid confining chambers for conducting reactions, each defined by two spaced-apart opposing walls, side walls connecting respective ones of said two opposing walls, and means permitting the introduction and removal of the liquid into and from each of the chambers, each of the chambers providing a major plane of liquid containment. The cuvette is improved in that the chambers are disposed such that the major plane of one of the chambers lies disposed above the major plane of the other chamber; whereby the length and/or width of the cuvette is reduced compared to a comparable cuvette in which the major planes are coplanar.

In accord with yet another aspect of the invention, there is provided a method of amplifying a nucleic acid sequence comprising the steps of treating a mixture of a separated strand of nucleic acid with a molar excess of an oligonucleotide primer at a temperature effective to attach the primer to the strand, heating the bound primer and strand in the presence of an extension enzyme to extend the primer to form a complementary strand, heating the bound complementary strand and the strand of nucleic acid at a temperature that causes them to separate into two template strands, and then repeating each of the previous steps on the template strands to produce many numbers of amplified strands.

The method is improved in that it further includes the steps of:

adding to the mixture a detection probe and a capture probe each comprising a complementary sequence of nucleotides that bond to an oligonucleotide sequence of choice and either a signal moiety capable of reacting to produce a detectable signal, or a capture moiety that will immobilize a strand bonded to the probe, respectively;

reacting the probes with the amplified strands to bind the probes to the amplified strands;

transferring a mixture containing the bound probes and strands to a separation medium;

and separating strands bearing capture probes on them from those lacking such probes, by passing the mixture through a filter containing a substance that binds with the capture moiety but which allows passage of strands lacking the capture moiety.

Thus, it is an advantageous feature of the invention that rapid thermal energy transfer occurs in and out of the cuvette and its liquid contents, permitting the liquid to undergo multiple temperature changes as needed for the desired reaction. As a result, a required number of repetitive cycles can be achieved in less time than has been heretofore possible.

It is a related advantageous feature of the invention that a cuvette is provided which allows rapid thermal processing of DNA strands through a multizoned cycle requiring many heat-and-cool repetitions.

It is still another related advantageous feature of the invention that such a cuvette and its liquid has a reduced thermal time constant, requiring very little delay just to heat up or cool down the liquid.

It is another advantageous feature of the invention that such a cuvette also permits relatively easy withdrawal of the complete liquid contents, once the reactions are complete.

Another advantageous feature of the invention is the provision of such a cuvette in which the contents can be readily sealed from exposure to the atmosphere.

Still another advantageous feature of the invention is the provision of such a cuvette with two chambers and with a minimum of length and width.

Other advantageous features will become apparent upon reference to the following detailed description of the preferred embodiments, when read in light of the attached drawings.

BRIEF DESCRIPTION OF THE DRAWINGS

FIG. 20 is a section view similar to FIG. 17, of still another embodiment; and

FIG. 21 is a section view taken generally along the line of XXI—XXI of FIG. 20.

DESCRIPTION OF THE PREFERRED EMBODIMENTS

The invention is described hereinafter preferably for temperature cycling over a range of at least 35° C., as is particularly useful in replicating DNA strands. In addition, it is also useful for any kind of reaction of liquid components and reagents that requires repetitive heating and cooling of the cuvette within the reaction is conducted.

Orientations such as "up", "down", "above" and "below" are used with respect to the cuvette as it is preferably used.

Figure 2:
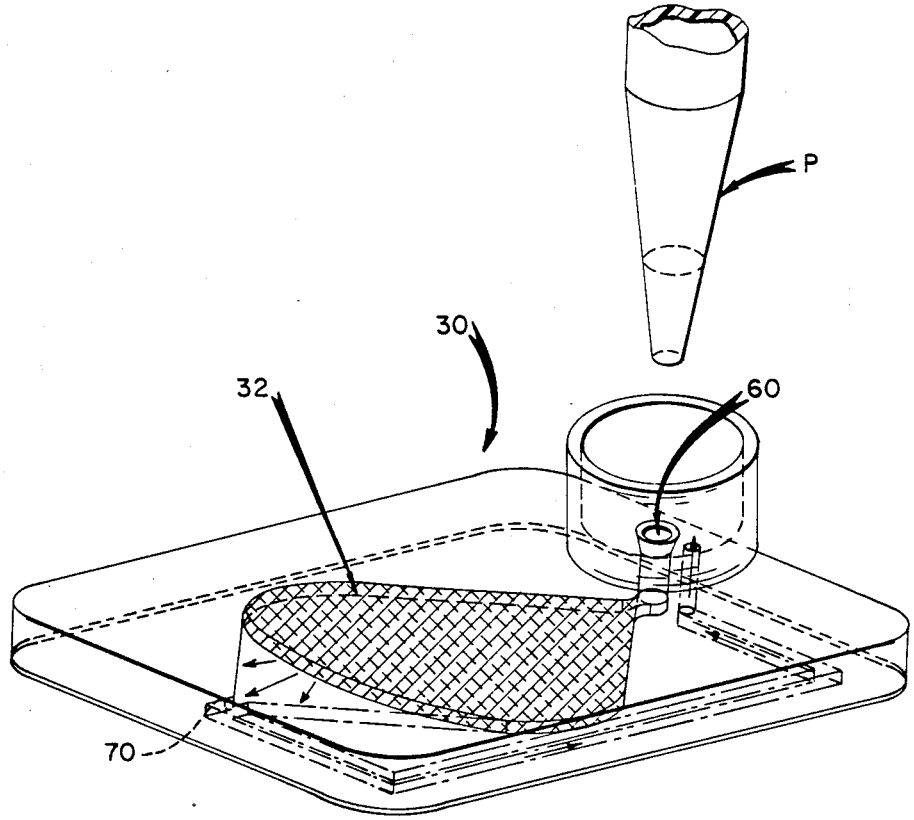
FIG. 2 is an isometric view of a cuvette prepared in accordance with the invention.
Figure 3:
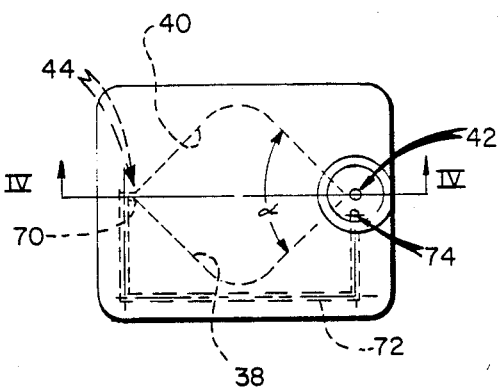
FIG. 3 is a plan view of the cuvette of FIG. 2.
Figure 4:
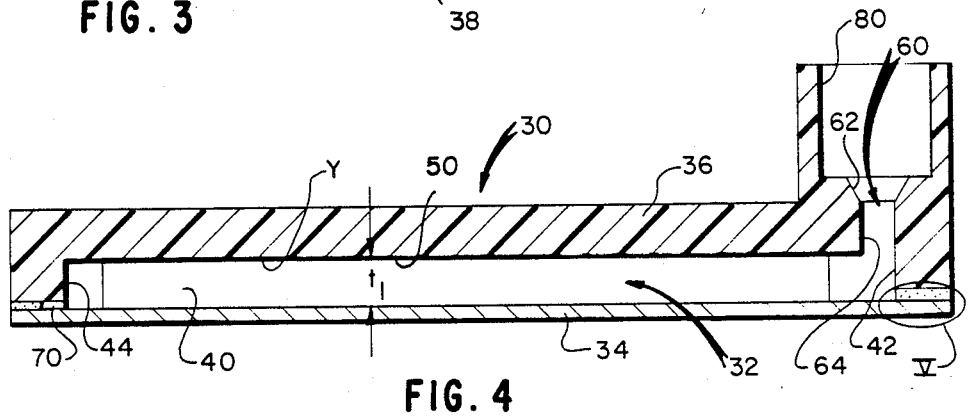
FIG. 4 is a section view taken generally along the line IV—IV of FIG. 3.

Turning first to FIGS. 2-4, a cuvette 30 constructed in accord with the invention comprises a liquid-confining chamber 32 defined by two opposing walls 34 and 36, FIG. 4, spaced apart a distance $t_1$. Such spacing is achieved by side walls 38 and 40, FIG. 3, that join at opposite ends 42 and 44 of chamber 32. Most preferably, the shape of side walls 38 and 40 is one of a gradual concavity, so that they diverge at end 42 at an angle alpha of about 90°, and at a point halfway between ends 42 and 44, start to reconverge again at an angle of about 90°. Distance $t_1$, FIG. 4, is selected such that such distance, when considered in light of the shape of sidewalls 38 and 40, minimizes the quantity of liquid that is retained in the cuvette upon removal of liquid. That is, it is well-known that capillary spacings resist liquid removal. Therefore, the thickness of the liquid between closely-spaced walls 34 and 36 is preferably a non-capillary spacing, namely a spacing $\geq 0.5$ mm and most preferably, 0.5 to 2.5 mm. More precisely, given a particular shape to the liquid container, the ability of the container to empty against such adverse factors as capillary attraction, can be expressed as a capillary number C. The equation is $N_{ca} = \mu \cdot V/\gamma$. In this equation, $\mu$ is viscosity, and for water solutions, this is about 0.01 centipose. $\gamma$ is surface tension, which for water solutions is about 70 dynes/cm. V is velocity in cm/sec, which is determined by the total volume to be emptied, divided by the flow-through area of the exit, and divided by the acceptable time of emptying. Therefore, the velocity factor requires detailed consideration.

The volume to be emptied varies from 200 to 100 $\mu$l. The acceptable times are from 1 to 10 secs. Thus, V ranges between 200/A.1 as a maximum and 100/A.10 as a minimum. For purposes of the invention, A is assumed to be about $5.2 \times 10^{-3}$ cm$^2$, the flow-through area of exit 60. Thus, V ranges between about 1.92 cm/sec and about 38.5 cm/sec. In turn, then, the capillary number for this cuvette is between about 0.0003 and about 0.006. However, this must be coupled with a non-capillary spacing, since only that spacing allows such a rate of emptying to occur.

Walls 34 and 36 provide the major surfaces in contact with the liquid. As such, their surface area is selected such that, when considered in light of the thickness of spacing $t_1$, the surface-to-volume ratio for chamber 32 is optimized for a high rate of thermal energy transfer. A highly preferred example is the exposed surface area of 2.4 cm$^2$ (0.37 in$^2$) for each of walls 34 and 36, with the surface from the side walls providing a contact area of about 0.36 cm$^2$. Most preferably, therefore, the surface-to-volume ratio is between about 65 in$^{-1}$ and about 130 in$^{-1}$ for a fill volume of between 200 and 100 $\mu$l, respectively.

Such a large fluid surface-to-volume ratio provides an advantage apart from a rapid thermal energy transfer. It also means that, for a given volume, a much larger surface area is provided for coating reagents. This is particularly important for reagents that have to be coated in separate locations on the surface to prevent premature mixing, that is, mixing prior to injection of liquid within the chamber. Also, a more effective dissolution occurs for those reagents when liquid is introduced.

Optionally, therefore, one or more reagent layers 50 can be applied to the interior surface of wall 36, FIG. 4, in a form that will allow the one or more layers to enter into a reaction with liquid sample inserted into chamber 32. Thus "a reagent" is a substance that will interact physically or chemically with the liquid sample. Such reagent layer can be applied in conventional ways, such as by spraying and drying. Such reagents can include a polymerase enzyme, salts, buffers and stabilizers. The coated layer may also include primer-pairs and dinucleotides necessary for replication.

A liquid access aperture 60 is formed in wall 36 adjacent end 42. The aperture has an upper portion 62 and a lower portion 64 that connects the upper portion with chamber 32. Preferably at least portion 62 is conical in shape, the slope of which allows a large number of different conical pipette designs P, FIG. 2, to mate therewith.

At opposite end 44, an air vent 70 is provided, in a manner similar to that described in U.S. Pat. No. 4,426,451. Most preferably, air vent 70 extends into a passageway 72, FIG. 3, that is routed back to a point adjacent end 42, where it terminates in opening 74 adjacent access aperture 60.

Figure 10:
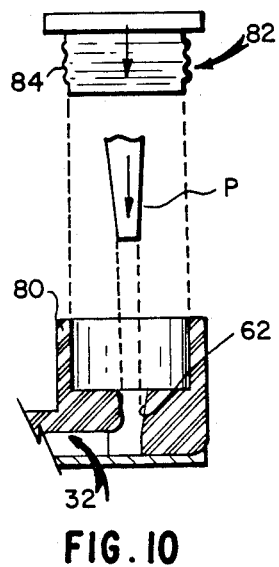
FIG. 10 is a fragmentary sectional view similar to FIG. 4, illustrating the cooperation of both a pipette and a seal, with the cuvette.

To allow a single closure device to seal both the access aperture 60 and opening 74 of the air vent, both of these are surrounded by a raised, cylindrical boss 80. Any conventional closure mechanism is useful with boss 80, for example, a stopper 82, FIG. 10. Such stopper can have external threads 84 for engaging mating internal threads, not shown, on the boss, or it can be constructed for a force fit within the boss 80.

Most preferably, except for wall 34 described below, the walls of the device are formed from less wettable materials, such as polycarbonate plastics.

Figure 5:
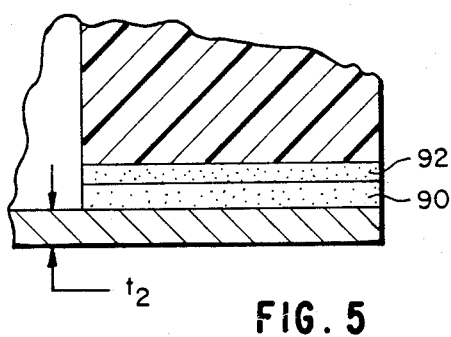
FIG. 5 is an enlarged, sectioned fragment taken from the encircled portion of the cuvette, labeled "V"

In accord with one aspect of the invention, the wall 34 opposite to wall 36 is constructed with a predetermined thermal path length and thermal resistance that will provide a high rate of thermal energy transfer. Most preferably, such path length ($t_2$ in FIG. 5) is no greater than about 0.3 mm, and the thermal resistance is no greater than about 0.01° C./watt. These properties are readily achieved by constructing wall 34 out of a metal such as aluminum that is about 0.15 mm thick. Such aluminum has a thermal resistance R, calculated as thickness $\chi$.1/(thermal conductivity K.surface area A), which is about 0.003° C./watt. (These values can be contrasted for ordinary glass of the same thickness, which has a thermal resistance of about 0.24° C./watt.)

Wall 34 can be secured to sidewalls 38 and 40 by any suitable means. One such means is a layer 90, FIG. 5, of a primer, which comprises for example a conventional high temperature acrylic adhesive, followed by layer 92 of conventional polyester adhesive. In some instances, layers 90 and 92 need not extend over the surface area of wall 34, as such would increase the thermal resistance of wall 34, and possibly interfere with reactions described within chamber 32. On the other hand, it will be apparent that some reactions can equally be adversely affected by metal ions present and for these reactions, the adhesive coats the entire surface area of wall 34.

A cuvette constructed as described above for FIGS. 2–4, has been found to produce a thermal time constant tau ($\tau$) for its contained liquid that is no greater than about 10 seconds. Most preferred are those in which $\tau$ is of the order of 3–8 seconds. That is, FIG. 6, when such a cuvette, filled with water, is heated along the exterior of wall 34, and its temperature is measured at point Y, FIG. 4, a thermal response curve is generated from 28° C. to a final temperature of 103.9° C. The time it takes for the liquid therein to reach a temperature of 76° C. (63% of the difference (103.9−28)) is the approximate value of tau ($\tau$). This derives (approximately) from the well-known thermal response equation:

Temperature T (t)=Final Temperature+(Initial Temperature−Final Temperature).$e^{-t/\tau}$   (1)

Thus, if the time interval t in question equals tau, then $e^{-t/\tau} = e^{-1} \approx 0.37$. In such a case, T (t) (at t=tau) is the temperature which is equal to the final temperature, plus 63% of (Initial Temperature−Final Temperature). (The step-wise shape of the data in FIG. 6 is an artifact of the recorder.)

Figure 6:
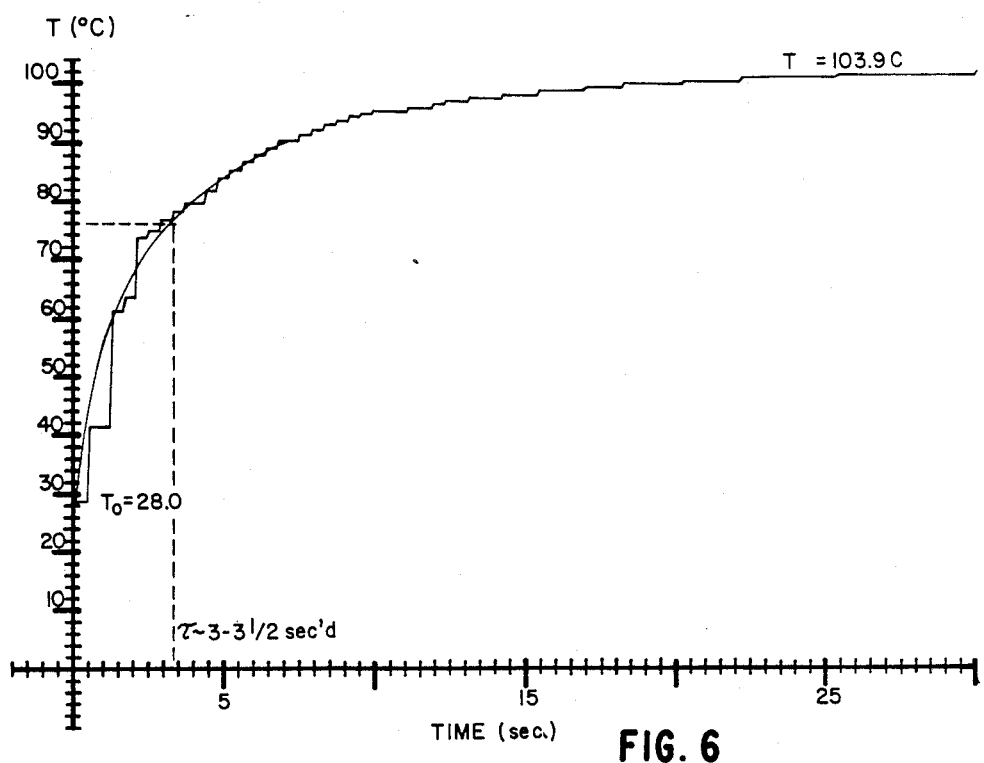
FIG. 6 is a plot of an actual time-temperature response of such a cuvette, to obtain the thermal time constant thereof.

Therefore, tau for the liquid of that cuvette is about 3.5 seconds (assuming that the response curve of FIG. 6 obeys the equation (1) above, which it does to a sufficiently close approximation).

If the adhesive of layers 90 and 92 does extend over all the surface of wall 34, then tau can be increased to as much as 7 or 8 sec.

Figure 1:
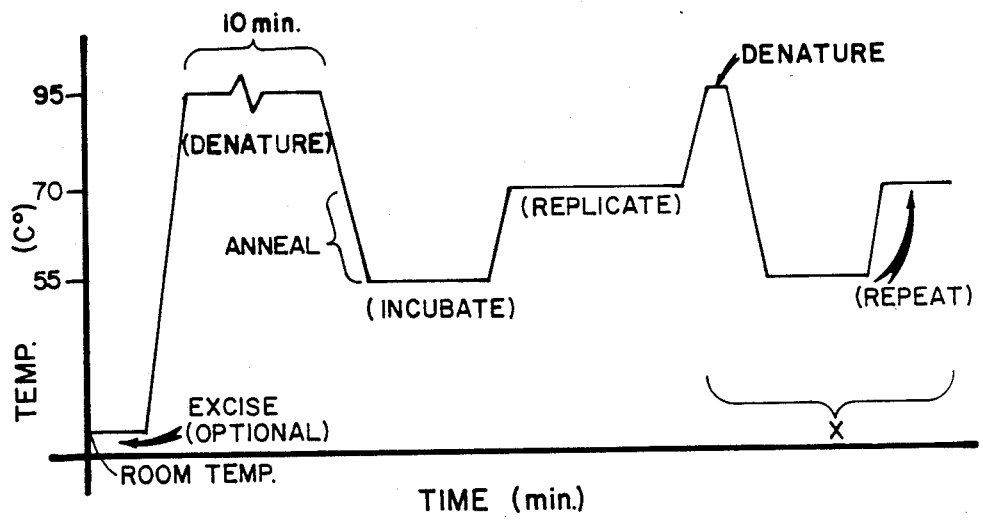
FIG. 1 is a graph plotting typical temperature changes for a cuvette in which DNA replication is occurring.
Figure 7:
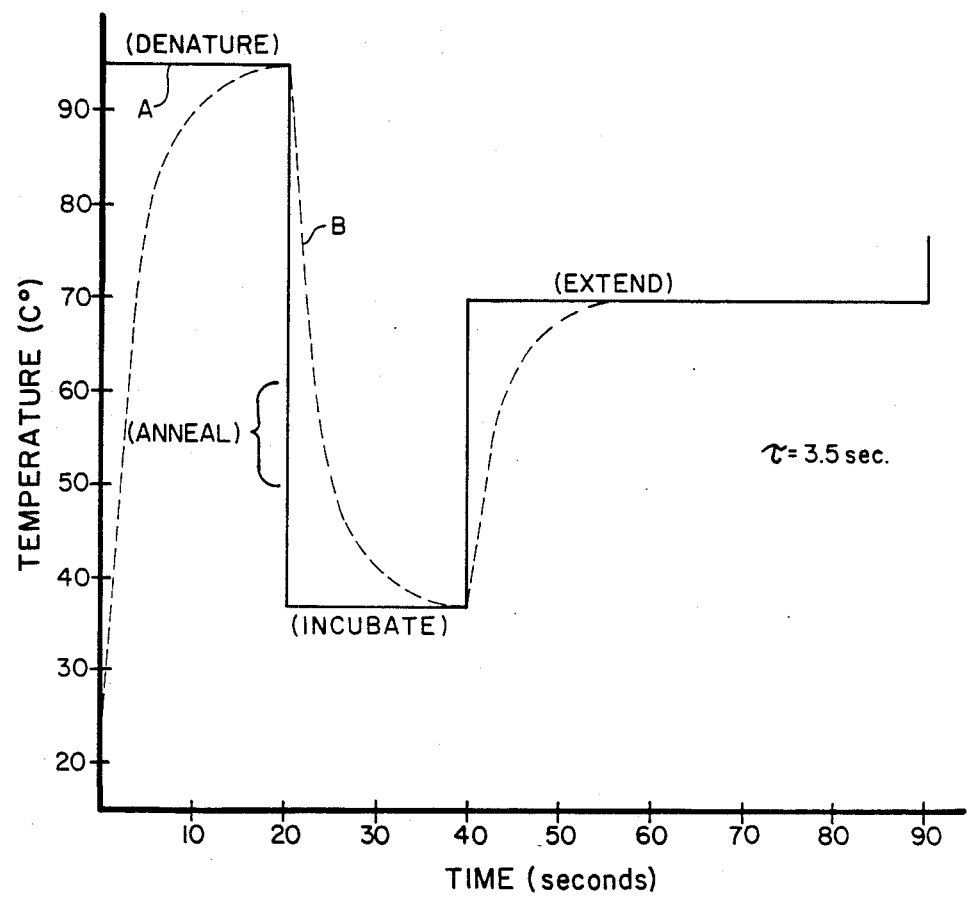
FIG. 7 is a plot of the heating response curve that such a cuvette will have, in light of the data of FIG. 6.

With a value of tau equal to about 3.5 sec, the thermal response curve of the same cuvette can be predicted under the conditions it will be subjected in accordance with the protocol of FIG. 1. FIG. 7 is such a response curve, generally for only the last segment of FIG. 1 marked "X", where the stepped portions "A" are the oven or incubator temperatures, and the curve "B" is the temperature of the liquid contents, for tau $\approx$3 seconds. (However, in this example, the incubation temperature was selected to be 37° C. instead of 55° C.).

As a comparative example, the cuvette described in U.S. Pat. No. 3,691,017 has the following properties. Its overall thickness (col. 8, lines 42–44) is 5/16" or 0.31". The space occupied by the liquid has a thickness of 5 mm (line 44, col. 8). The window is ½" by ¼" (line 45), so that the volume of the liquid of a unit area of one square inch, is estimated to be about 0.197 in $^3$, and its surface area contacting the cuvette is estimated to be about 2.79 in $^2$. This produces at best a surface/volume ratio of only about 14.2 in $^{-1}$. A sphere of the same volume has a S/V ratio of 8.3 in $^{-1}$, indicating that the cuvette is only slightly better in its S/V ratio than the worst possible configuration (the sphere). In addition, the heating element is a foil of aluminum that has to extend into the cavity from the outside, thus producing a thermal path length well in excess of 1 mm. All of this clearly indicates that the thermal time constant tau of water in such a cuvette is substantially greater than 10 sec.

Figure 8:
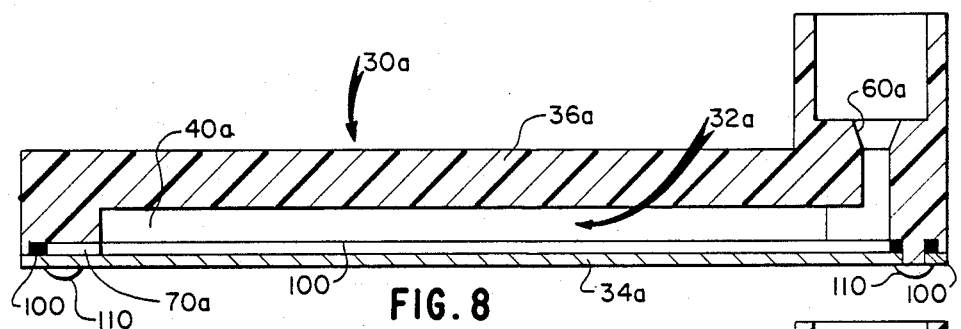
FIGS. 8 and 9 are sectional views similar to that of FIG. 4, but illustrating two different embodiments.

It is not necessary that the cuvette be assembled using adhesive. A non-adhesive embodiment is illustrated in FIG. 8, wherein parts similar to those used in the previous embodiment bear the same reference numeral to which is appended the letter "a". Thus, cuvette 30$a$ comprises two opposed walls 34$a$ and 36$a$ which, with side walls (of which only 40$a$ is shown), define a chamber 32$a$. A liquid access aperture 60$a$ and an air vent 70$a$ are provided, also as in the previous embodiment, and wall 34$a$ has the same properties as discussed above. However, in this embodiment there are no adhesive layers between wall 34$a$ and side wall 40$a$ at any point. Instead, around the entire edge of chamber 32$a$, there is a gasket seal 100 of an elastomer, or other suitable gasket material, between wall 34$a$ and the side wall. In addition, bumps of plastic 110 extend from the side walls through appropriate openings in the wall 34$a$. Bumps 110 are then upset by heat or pressure to rivet wall 34$a$ in place. Optionally, gasket seals 100 can also extend around such bumps.

Figure 9:
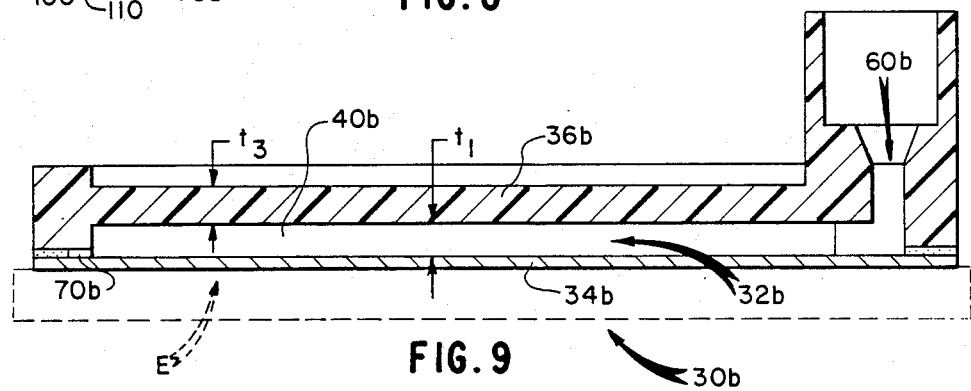

When the access aperture and the air vent are sealed, and the cuvette is heated, pressure builds within chamber 32 and 32$a$. It is preferred, therefore that a part of the cuvette, other than the thermally conductive wall, become deformed to accommodate the pressure increase, in order to maintain intimate contact between reaction vessel wall 34 and the incubator. Still further, deformation of some other wall reduces the strain on the seal that holds the thermally conductive wall in place. Such an embodiment is shown in FIG. 9, as described and claimed in the commonly owned application Ser. No. 123,752, filed Nov. 23, 1987, entitled "Cuvette with Non-Flexing Thermally Conductive Wall" filed by Helfer et al. Parts similar to those previously described bear the same reference numeral, to which the distinguishing suffix "b" is appended.

Thus, cuvette 30$b$ comprises opposed walls 34$b$ and 36$b$ defining, with side walls 40$b$ (only one shown), a chamber 32$b$ having a spacing $t_1$. These and the access aperture 60$b$ and air vent 70$b$ are constructed as in either of the previous embodiments. However, to insure that wall 34$b$ does not deform under pressure, wall 36$b$ is constructed to have a flexure strength that is less than that of wall 34$b$. Specifically, this is preferably done as follows: if wall 34$b$ comprises aluminum that is about 0.15 mm thick, then its flexure strength K at the center of flexure is determinable, based on the following:

Deflection X is determined by the well-known equation $$X = \alpha P a^2 / E t^3 \quad (2)$$

where P=total applied load, E=plate modulus of elasticity, t=plate thickness, a=the length of one side of the plate (here, the flexing wall), and $\alpha$ is an emperical coefficient (usually equal to about 0.015). Rearranging, $$P/X = E t^3 / \alpha a^2 \quad (3)$$

Because P/X is analogous to F/X which equals K, then $$K \approx E t^3 / \alpha a^2 \quad (4)$$

This allows K to be calculated to be about $6.11 \times 10^6$ dynes/mm. For wall 36b to have a flexure strength less than that, it need only comprise a layer of polyethylene or polypropylene that is about 0.3 mm thick (thickness $t_3$ that is twice that of the aluminum wall 34b), to have a flexure strength of about $8.3 \times 10^5$ dynes/mm, calculated in the same manner. In such a construction, wall 36b will dome upwardly as pressure is generated within chamber 32b, leaving wall 34b lying planar against the heating element (shown in phantom as "E").

In use, any of the above-described embodiments is filled to about point 44, FIG. 3, which provides a fill of about 90%, with a liquid containing the desired sample for reaction, for example, a solution of a DNA sequence that is to be amplified. The device is then inserted into an appropriate incubator and cycled through the necessary stages for the reaction.

In accord with another aspect of the invention, a movable valve is disposed to selectively open and close access to the chamber within the cuvette. Parts similar to those previously described bear the same reference numeral to which the distinguishing letter "c" has been appended.

Figure 11:
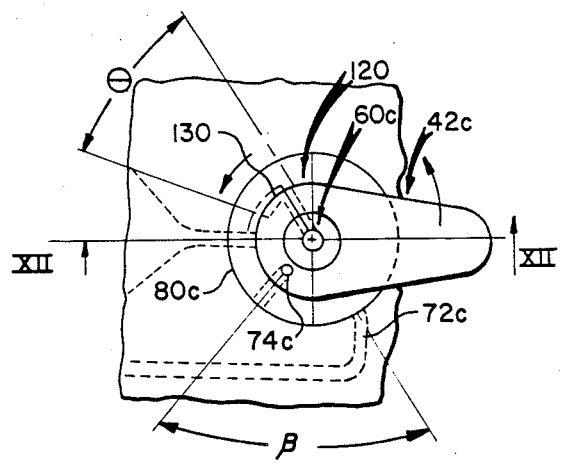
FIG. 11 is a fragmentary plan view of an alternate embodiment, particularly of the valving mechanism.

Thus, in FIGS. 11-14, end 42c of chamber 32c has both the liquid access aperture 60c and the air vent passageway 72c located adjacent to each other, within raised boss 80c, FIG. 11. Upper portion 62c is conically shaped, as in previous embodiments, to allow a mating engagement of pipette P, FIG. 12.

Figure 12:
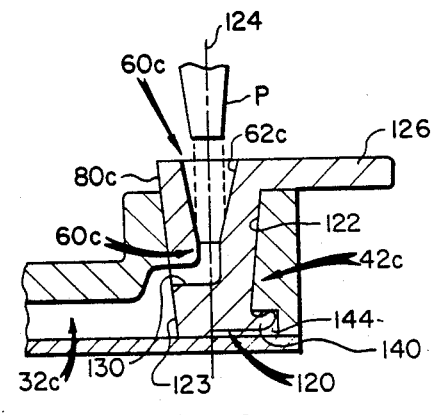
FIG. 12 is a section view taken generally along the line XII—XII of FIG. 11.
Figure 13:
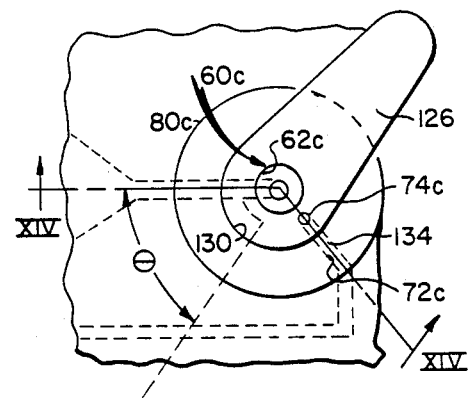
FIG. 13 is a fragmentary plan view similar to that of FIG. 11, but with the valve rotated about 45°.
Figure 14:
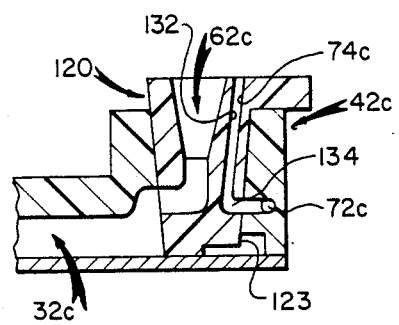
FIG. 14 is a section view similar to FIG. 12, but illustrating the valve rotated as noted for FIG. 13, and taken along the line XIV—XIV of FIG. 13.

However, in this embodiment a valve is provided, comprising a rotatable portion 120 mounted within a mating conically shaped aperture 122, FIG. 12. Rotatable portion 120 has an exterior, conically shaped surface 123. The valve has an axis of rotation 124, preferably concentrically disposed within aperture 60c. A handle 126 permits manual or automated rotation of the valve. Both the access aperture 60c, as well as air vent opening 74c, are located in the movable valve portion 120, FIGS. 11 and 13.

To selectively connect aperture 60c and opening 74c to chamber 32c, two paths are formed in rotatable portion 120. Path 130 extends from aperture 60c to the exterior surfaces 123, FIG. 12, where it is open over an angle theta of that surface, FIG. 11. Path 132 extends, FIG. 14, from aperture 74c to an exit 134 on surface 123. The heights of the paths 130 and 132, relative to the chamber 32c and passageway 72c, respectively, are such as to allow the paths to be fluidly connected to the chamber or passageway, when rotatable portion 120 is rotated to the position shown in FIG. 13. In addition, because of the angle theta of access provided by path 130, portion 120 can be rotated also to a position (not shown) wherein only the access aperture 60c is in fluid communication with chamber 32c, if desired.

A tail portion 140 holds rotatable portion 120 vertically in place, and rides in a slot 144, FIG. 12.

The access and air vent valve need not be rotatable. Translatable valves are also useful. Parts similar to those previously described bear the same reference numeral to which the distinguishing suffix "d" is appended.

Figure 15:
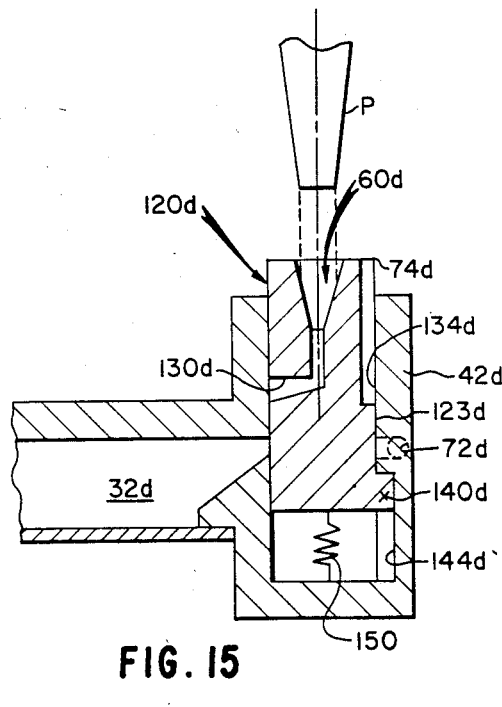
FIG. 15 is a section view similar to that of FIG. 12, but of still another embodiment.

Thus, in FIG. 15, valve portion 120d is disposed at end 42d so as to incorporate both the access aperture 60d and air vent opening 74d. However, unlike the previous embodiment, portion 120d is vertically, translatably mounted, with tail portion 140d riding vertically in a slot 144d that permits no rotation. A spring 150 biases portion 120d so that, normally, it is raised to misalign paths 130d and 134d with respect to chamber 32d and vent passageway 72d, respectively, thus sealing off chamber 32d from the outside environment. To access the chamber, the user need only press down on portion 120d, such as by engaging access aperture 60d with a pipette P, and push against spring 150.

Vent opening 74d is, in this embodiment, a groove formed in exterior surface 123d, which allows venting of passageway 72d when portion 120d is pushed down a distance sufficient to fluidly connect chamber 32d also with aperture 60d.

Figure 16:
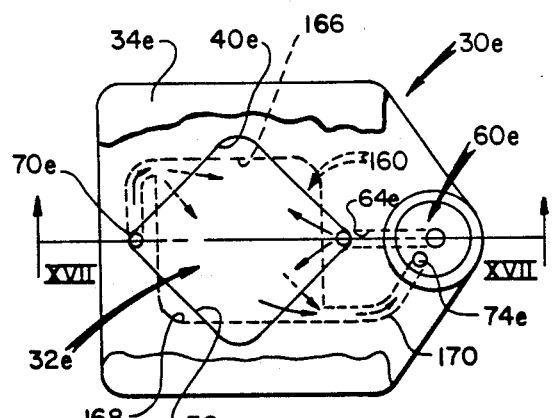
FIG. 16 is a plan view of another embodiment of the invention partially broken away.
Figure 17:
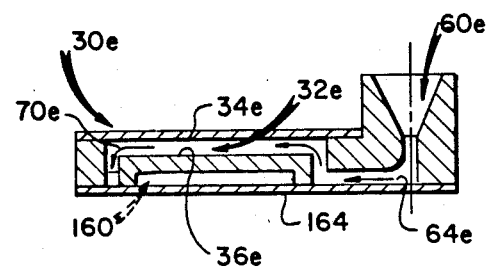
FIG. 17 is a section view taken generally along the line XVII—XVII of FIG. 16.

In certain reactions, it is desirable that the liquid be moved to a second chamber, after an appropriate residence time in the first chamber. For example, DNA probe assays require a single, additional, new thermal cycle with which to bond DNA probes to the amplified target sequence. Subsequent to the DNA amplification temperature cycling discussed above, the DNA-bearing broth is brought into contact with DNA probes specific to the amplified target sequence. Such probes can be coated onto the walls of a reaction vessel, and more specifically, on the walls of a second, DNA probe bearing chamber, as shown in FIGS. 16-17. Parts similar to those previously described, bear the same reference numeral to which the distinguishing suffix "e" is appended.

Thus, cuvette 30e comprises chamber 32e disposed between two opposing walls 34e and 36e, FIG. 17, having major surfaces, and side walls 38e and 40e, FIG. 16, all of which are generally similar to previous embodiments, with an access aperture 60e, air vent 70e and air vent opening 74e. However, unlike the previous embodiments, metallic wall 34e is above, rather than below, chamber 32e, FIG. 17, so that heat is applied downwardly from above cuvette 30e. (A filter membrane, not shown, can be optionally positioned at 70e.)

This rearrangement of walls 34e and 36e is due to the fact that a second chamber 160 is provided, disposed underneath chamber 32e. That is, each of the two chambers provides a major plane of liquid containment, and preferably, has a generally planar configuration due to the opposing walls of primary surface area being also generally planar and respectively coplanar. Thus, the major containment plane of chamber 32e is disposed above the major containment plane of chamber 160.

As is apparent in FIG. 17, chamber 160 has an opposing, primary surface wall that is in fact wall 36e. The opposite wall 164 is the wall that provides the thermal energy transfer, by being constructed substantially the same as wall 34e. Side walls 166 and 168, FIG. 16, shape the chamber 160 as in the case of chamber 32e, except that chamber 160 is rotated about 45° with respect to chamber 32e, so that its air vent, described below, does not conflict with the lower portion 64e of access aperture 60e.

An air vent and passageway 170 is provided for chamber 160, FIG. 16. It is constructed similar to the air vent passageway of the air vent of previously embodiments. Alternatively, not shown, air vent opening 74e can be shaped and positioned to allow direct removal of liquid from chamber 160, without requiring it to be withdrawn back through chamber 32e as shown in FIG. 16.

In use, liquid in chamber 32e is forced to flow into chamber 160, as per the arrows in FIG. 17, by injecting either air pressure into chamber 32e through the access aperture, or, e.g., solutions optionally containing reagents for further reaction in the cuvette, or by pulling a vacuum on chamber 160.

Alternatively, the two chambers can overlie each other with side walls that are exactly aligned, rather than offset by 45°. This embodiment is shown in FIG. 18, wherein parts similar to those previously described bear the same reference numeral to which the distinguishing letter "f" is appended.

Thus, cuvette 30f comprises upper and lower chambers 32f and 160f, sharing a common wall 36f that is not a thermal transfer wall. Air vent 70f feeds liquid from chamber 32f to 160f, and walls 34f and 164f provide the necessary rapid transfer to thermal energy. Unlike the previous embodiment, however, sidewalls (40f of chamber 32f being shown) are aligned with the sidewalls of chamber 160f (wall 166f being shown). This is rendered possible by rotating boss 80f 90° so as to provide access aperture 60f that is totally within the major plane of liquid confined by chamber 32f. In such a cuvette, air vent 170f and its opening 74f are located within the major plane of liquid confined within chamber 160f.

Figure 18:
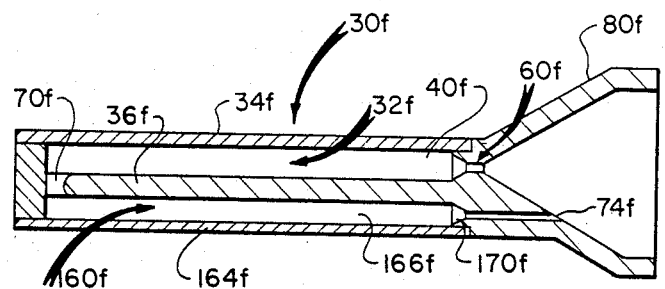
FIG. 18 is a section view similar to that of FIG. 17, but illustrating yet another embodiment.

In each of the two embodiments of FIGS. 16–18, the advantage achieved is that the length or width of the cuvette is not extended appreciably beyond that of the cuvette of FIG. 2, as it would be if the two major planes of liquid confinement were coplanar. Only the vertical thickness is slightly increased to permit the two chambers to be vertically stacked to provide a three-dimensional flow.

Yet another useful configuration is one shown in FIGS. 20 and 21, in which a third liquid-confining chamber is fluidly connected to said second chamber, with a liquid-permeable membrane isolating and separating the third chamber from the second chamber. Parts similar to those previously described bear the same reference numeral, to which the distinguishing suffix "g" is appended.

Thus, cuvette 30g comprises a first chamber 32g having opposing walls 34g and 36g (of which wall 34g is metallic), sidewalls 38g and 40g (FIG. 21) and access aperture 60g. Chamber 32g leads via passageway or air vent 70g to the second chamber 160g, disposed in a major plane of configuration that is parallel to that plane of configuration occupied by chamber 32g, as in the embodiment of FIG. 16. However, in this embodiment, chamber 160g is above chamber 32g, rather than below it. Chamber 160g is defined in part by opposing walls 162g and 136, with wall 136 being preferably a buckling, preferably transparent, wall as in the case of wall 36b in the embodiment of FIG. 9. Wall 136 is also preferably recessed below surface 137, so as to protect the exterior surface of wall 136 from scratching. Chamber 160g is also defined by a liquid-permeable membrane 300 having an upper surface 302 facing into chamber 160g. A lower surface 304 of the membrane faces away from chamber 160g. Useful materials for this membrane include cast, woven or electro-optically machined, microfiltration membranes. Sidewalls 166g and 168g, FIG. 21, complete that chamber.

A third chamber 310 is fluidly connected to chamber 160g via membrane 300, so that chamber 310 is isolated and separated from the other two chambers by the membrane. Preferably, chamber 310 is formed within the block located between walls 36g and 162g, FIG. 20, so that the three chambers form a vertical stack, downwardly, of chamber 160g, 310 and 32g. Air vent passageway 170g leads from chamber 310 to air vent opening 74g located within boss 80g, as in previous embodiments. In addition, an air vent (not shown) containing a liquid-impermeable but air-permeable plug, extends from chamber 160g to boss 80g, in a location that is generally above passageway 170g.

Most preferably, a liquid-absorbing material 320 is disposed within chamber 310, to fill the chamber and preferably contact lower surface 304 of membrane 300.

A preferred use of cuvette 30g is to trap and identify a particular nucleic acid sequence, such as of DNA, amplified within the cuvette. To this end, surface 302 preferably includes means for capturing proteinaceous materials capable of bonding to a DNA strand. Such capture proteins are conventional and comprise a complementary sequence of nucleotides that bond to the DNA sequence of choice, the sequence having attached to it any appropriate means for bonding to the membrane. For example, such bonding means can be one of a pair of avidin and biotin, as is conventional. The other of the pair is bonded to surface 302.

The method of use of cuvette 30g will be apparent from the preceding, and generally is as follows:

Chamber 32g contains in pre-prepared form most or all of the reagents needed for DNA amplification. The DNA-containing liquid is injected via pipette P, to only partially fill chamber 32g, and cap C is screwed into place or otherwise attached. Denaturing, incubating, and replicating proceed as in the other embodiments. Subsequently, pipette P is used again to inject into chamber 32g, the capture probes discussed above, and also detection probes. Such detection probes are also conventional, and comprise a protein and complementary nucleotides that attaches to the DNA strand of choice opposite to the end to which the capture probe attaches. The detection probe also includes any appropriate signal-generating moiety, for example, horseradish peroxidase, capable of reacting with a leuco dye to produce a detectable signal (e.g., a color change.) The technology for attaching two different probes at the opposite 3' and 5' end is known. For example in "Efficient Methods for Attachment of Thiol Specific Probes to the 3' End of Synthetic Oligodeoxyribonucleotides", Vol. 15 of *Nucleic Acids Research*, p. 5305 (1987), the techniques useful for the 3' end attachment are discussed. The articles discussing 5' end attachment are legion, for which the following is only representative: "Introduction of 5' Terminal Functional Groups. . . . ", Vol. 164 of *Analytical Biochemistry*, p. 336 (1987). It will be readily apparent that either the 3' or the 5' end is used to attach one of the two probes, and the other end is used to attach the other of the two probes.

Alternatively, the detection probe and the immobilizing probe can be one and the same, attached at, say, just the 5' end, using the techniques taught in the aforesaid *Analytical Biochemistry* article.

The cuvette, now containing both probes as well as the amplified DNA, is agitated or shaken, to promote mixing.

Thereafter, portion "X" of the cycle shown in FIG. 1 is repeated in order to cause the two probes to attach to separate strands of DNA.

Following this step, the liquid, still in chamber 32g, is pushed up passageway 70g into chamber 160g. This pushing step is achieved by injecting via pipette P either additional liquid, or air, or by pulling a vacuum at vent opening 74g. If a liquid is used, a neutral solution (containing no active ingredients) is used. The liquid is allowed to incubate in chamber 160g, preferably by closing off vent opening 74g with cap C.

Thereafter, all the liquid is drawn off through membrane 300 into absorbing material 320. This is done either by an additional pulse of air being injected, by assisting the natural flow of liquid through membrane 300 by applying a partial vacuum to opening 74g or by capillary attraction of absorbant material 320. At this point, the capture and detection probes have bonded, as a result of the replication part of portion X of the cycle, to the DNA strand, and the capture probe is captured by the surface 302 of the membrane. Any DNA strands lacking the capture probe pass through membrane 300 and are absorbed by material 320.

The final step is to inject into chambers 32g and 160g, a liquid containing a leuco dye or some other substance capable of reacting with the detection probe projecting from the DNA strands captured on surface 302. Useful leuco dyes include those set forth in U.S. Pat. No. 4,089,747, preferably in combination with a solubilizing polymer such as poly(vinyl pyrrolidone). A preferred example of the dye is 2-(4-hydroxy-3,5-dimethoxyphenyl)-4,5-bis(4-methoxyphenyl)imidazole, since this gives about 1000 dye molecules per 1 molecule of horse radish peroxidase.

As an alternative to the above, capture probes bounded to beads, also conventional, can be used. The beads are selected with a diameter that is too large to pass through the pores of membrane 300.

Figure 19:
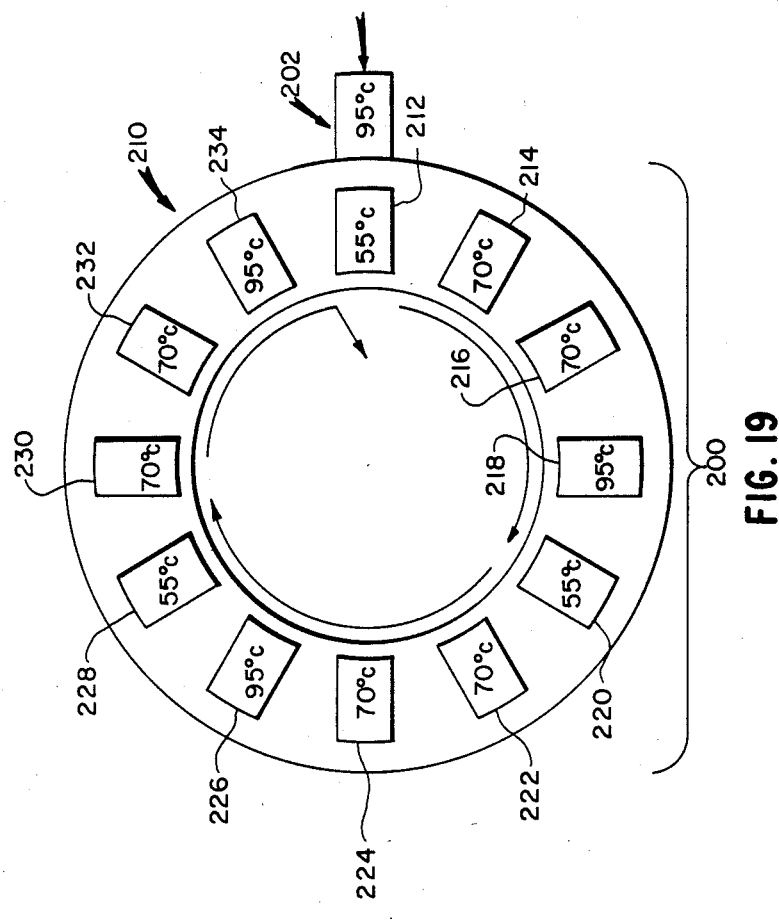
FIG. 19 is a schematic illustration of an incubating apparatus that is useful in cycling the cuvette through its DNA processing temperatures.

Any suitable incubator is useful to cycle the cuvettes of this invention through the desired heating and cooling stages. Most preferably, the incubator provides stages that cycle through the temperatures shown in FIG. 1. A convenient incubator 200 for doing this is one having the stations shown in FIG. 19. A preincubate station 202 has heating means that establishes a temperature of approximately 95° C. From here, the cuvette is pushed by conventional pusher means onto a ring 210 of constant temperature stations, the first one 212 of which is maintained at 55° C. From this station the cuvette is shuttled to station 214, which heats it to 70° C. This temperature is maintained for a period, and accordingly station 216 is also at that temperature. Next, a short-time denaturing station 218 is encountered to denature the newly replicated DNA, which station is maintained at 95° C. Stations 220–234 simply repeat twice more the cycles already provided by stations 212–218. After station 234 is encountered, and if all amplication is complete, a conventional transfer mechanism (not shown) moves the cuvette off ring 210 for further processing. (Both the injection of liquid into the cuvette and the removal of liquid therefrom are done off-line, that is, outside of incubator 200.) If further amplification is needed, a particular cuvette continues around the incubator for additional cycles.

The invention has been described in detail with particular reference to preferred embodiments thereof, but it will be understood that variations and modifications can be effected within the spirit and scope of the invention.

What is claimed is:

1. In a thermal cycling cuvette for controlled reaction of components of a liquid involving cycling through a temperature range of at least about 35° C., said cuvette having at least one liquid-confining chamber defined by two spaced-apart opposing walls each providing a major surface of contact, side walls connecting said two opposing walls, and means permitting the introduction of liquid into, and the removal of such liquid from, said chamber;

the improvement wherein said opposing walls and said side walls are dimensioned to provide (a) a spacing between said opposing walls of no less than 0.5 mm and (b) a predetermined surface-to-volume ratio of said chamber, at least one of said opposing walls being provided with a predetermined thermal path length and thermal resistance such that said ratio, path length and thermal resistance are effective to provide, for pure water contained within said chamber in contact with said opposing walls, a thermal time constant for such water that is no greater than about 10 seconds, for a liquid volume of no more than about 200 μl.

2. In a thermal cycling cuvette for controlled reaction of components of a liquid involving cycling through a temperature range of at least about 35° C., said cuvette having at least one liquid-confining chamber defined by two spaced-apart opposing walls, side walls connecting said two opposing walls, and means permitting the introduction and removal of such liquid, into and from said chamber, the improvement wherein said opposing walls and said side walls are dimensioned to provide said chamber with an effective temperature controlled surface-to-volume ratio that is between about 65 in$^{-1}$ and about 130 in$^{-1}$ for a fill volume of between 100 and 200 μl, and at least one of said opposing walls having a thermal path length of no more than about 0.3 mm and a thermal resistance of no more than about 0.01° C./watt, whereby the cuvette has a maximized rate of heat transfer during heating and cooling cycles.

3. A cuvette as defined in claim 2, wherein said opposing walls and said side walls are spaced so that water can be effectively withdrawn in no longer than 10 seconds with a capillary number of less than 0.05.

4. A cuvette as defined in claim 3, wherein said distance of spacing of said opposing walls is from about 0.5 mm to about 2.5 mm.

5. A cuvette as defined in claim 1 or 3, wherein the structural component of at least one of said opposing walls comprises aluminum no thicker than about 0.15 mm.

6. A cuvette as defined in claim 1 or 3, wherein at least one entire surface of one of said opposing walls of said chamber has a thermal resistance of no more than about 0.01° C./watt.

7. A cuvette as defined in claim 1 or 3, and further including a reagent coated over at least one of said opposing walls.

8. A cuvette as defined in claim 7, wherein said one opposing wall is opposite to said opposing wall having said thermal path length.

9. A cuvette as defined in claim 1 or 3, wherein said permitting means includes means defining a liquid access aperture.

10. A cuvette as defined in claim 9, and further including an opening constructed to be larger than said liquid access aperture, to receive closure means for sealing said larger opening, and wherein said aperture is located within said larger opening.

11. A cuvette as defined in claim 10, and further including an air vent for said chamber.

12. A cuvette as defined in claim 11, wherein said air vent terminates at a location within said larger opening.

13. A cuvette as defined in claim 9, wherein said liquid access aperture is configured to removably mate with a pipette or pipette tip.

14. A cuvette as defined in claim 1 or 3, wherein said permitting means includes a liquid access aperture, an air vent, and a movable valve for selectively sealing off fluid flow between (a) each of said access aperture and air vent, and (b) said chamber.

15. A cuvette as defined in claim 14, wherein a portion of said valve is rotatably mounted in the cuvette, and further including means for rotating said valve portion about an axis, said access aperture and said air vent being rotationally oriented about said axis to cooperate with rotation of said valve portion to open and close said access aperture and said air vent.

16. A cuvette as defined in claim 14, wherein a portion of said valve is translatably mounted in the cuvette, and further includes biasing means for biasing said valve portion to a position that seals off said chamber from the exterior of the cuvette.

17. A cuvette as defined in claims 1 or 3, and further including a second liquid-confining chamber defined by two spaced-apart opposing walls with a relatively high exposed surface-to-thickness ratio, side walls connecting said second-chamber two opposing walls, means permitting the introduction of liquid into said second chamber from said first chamber, and means permitting the removal of such liquid out of said second chamber; said chambers further providing a major plane of liquid containment, the major plane of one of said chambers being disposed above the major plane of the other of said chambers.

18. A cuvette as defined in claim 17, and further including a third liquid-confining chamber fluidly connected to said second chamber, and a liquid-permeable membrane separating said third chamber from said second chamber.

19. A cuvette as defined in claim 18, and further including a liquid-absorbing material in said third chamber.

20. A cuvette as defined in claim 18, and further including on said membrane, means for capturing a proteinaceous material capable of bonding to a DNA strand.

21. A cuvette as defined in claim 20, wherein said capturing means includes either avidin or biotin, said proteinaceous material having bonded thereto, the other of the avidin/biotin pair.

22. A cuvette as defined in claim 1 or 3, wherein one of said walls is transparent and is recessed to protect it from scratches.

23. In a cuvette for controlled reaction of components of a liquid, said cuvette having first and second liquid confining chambers for conducting reactions, each defined by two spaced-apart opposing walls, side walls connecting respective ones of said two opposing walls, and means permitting the introduction and removal of such liquid into and from each of said chambers, each of said chambers providing a major plane of liquid containment;

the improvement wherein said chambers are disposed such that said major plane of one of said chambers lies disposed above the major plane of the other of said chambers;

and further including a third liquid-confining chamber fluidly connected to said second chamber, and a liquid permeable membrane separating said third chamber from said second chamber.

24. A cuvette as defined in claim 23, and further including a liquid-absorbing material in said third chamber.

25. A cuvette as defined in claim 23, and further including on said membrane, means for capturing a proteinaceous material capable of bonding to a DNA strand.

26. A cuvette as defined in claim 25, wherein said capturing means includes either avidin or biotin, said proteinaceous material having bonded thereto, the other of the avidin/biotin pair.

* * * * *